United States Patent
Meral et al.

(10) Patent No.: US 11,766,244 B2
(45) Date of Patent: Sep. 26, 2023

(54) SHEAR WAVE AMPLITUDE RECONSTRUCTION FOR TISSUE ELASTICITY MONITORING AND DISPLAY

(71) Applicant: KONINKLIJKE PHILIPS N.V., Eindhoven (NL)

(72) Inventors: Faik Can Meral, Mansfield, MA (US); Shriram Sethuraman, Lexington, MA (US); William Tao Shi, Wakefield, MA (US); Pingkun Yan, Gaithersburg, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 254 days.

(21) Appl. No.: 17/051,829

(22) PCT Filed: May 1, 2019

(86) PCT No.: PCT/EP2019/061156
§ 371 (c)(1),
(2) Date: Oct. 30, 2020

(87) PCT Pub. No.: WO2019/211336
PCT Pub. Date: Nov. 7, 2019

(65) Prior Publication Data
US 2021/0113192 A1    Apr. 22, 2021

Related U.S. Application Data

(60) Provisional application No. 62/741,905, filed on Oct. 5, 2018, provisional application No. 62/666,348, filed on May 3, 2018.

(51) Int. Cl.
*A61B 8/08*    (2006.01)
*G16H 50/50*    (2018.01)
(Continued)

(52) U.S. Cl.
CPC .............. *A61B 8/485* (2013.01); *A61B 8/463* (2013.01); *A61B 8/469* (2013.01); *A61B 8/5223* (2013.01);
(Continued)

(58) Field of Classification Search
CPC ......... A61B 8/485; A61B 8/463; A61B 8/469; A61B 8/5223; A61B 8/5246; A61B 8/587;
(Continued)

(56) References Cited

U.S. PATENT DOCUMENTS

| | | | |
|---|---|---|---|
| 2005/0004466 A1* | 1/2005 | Hynynen | G01S 15/8977 600/449 |
| 2005/0215899 A1 | 9/2005 | Trahey et al. | |

(Continued)

FOREIGN PATENT DOCUMENTS

| | | |
|---|---|---|
| WO | 2016001783 A1 | 1/2016 |
| WO | 2016156540 A1 | 10/2016 |
| WO | 2017211757 A1 | 12/2017 |

OTHER PUBLICATIONS

Paparo et al., Real-Time Elastography in the Assessment of Liver Fibrosis: A Review of Qualitative and Semi-quantitative Methods for Elastogram Analysis, Ultrasound in Medicine & Biology vol. 40, Issue 9, Sep. 2014, pp. 1923-1933, https://doi.org/10.1016/j.ultrasmedbio.2014.03.021 (Year: 2014).*

(Continued)

*Primary Examiner* — John Denny Li

(57) ABSTRACT

The present disclosure describes ultrasound systems and methods configured to determine the elasticity of a target tissue. Systems can include an ultrasound transducer configured to acquire echoes responsive to ultrasound pulses transmitted toward the tissue, which may include a region of increased stiffness. Systems can also include a beamformer (Continued)

configured to control the transducer to transmit a push pulse into the tissue, thereby generating a shear wave in the region of increased stiffness. The beamformer can be configured to control the transducer to emit tracking pulses adjacent to the push pulse. Systems can further include a processor configured to determine a displacement amplitude of the shear wave and based on the amplitude, generate a qualitative tissue elasticity map of the tissue. The processor can combine the qualitative map with a quantitative map of the same tissue, and based on the combination, determine a boundary of the region of increased stiffness.

15 Claims, 11 Drawing Sheets

(51) Int. Cl.
| | |
|---|---|
| G16H 30/40 | (2018.01) |
| A61B 8/00 | (2006.01) |
| A61B 18/00 | (2006.01) |
| A61B 18/12 | (2006.01) |

(52) U.S. Cl.
CPC ............ *A61B 8/5246* (2013.01); *A61B 8/587* (2013.01); *G16H 30/40* (2018.01); *G16H 50/50* (2018.01); *A61B 8/085* (2013.01); *A61B 18/12* (2013.01); *A61B 2018/00577* (2013.01)

(58) Field of Classification Search
CPC .................... A61B 8/085; A61B 18/12; A61B 2018/00577; G16H 50/50; G16H 30/40
See application file for complete search history.

(56) References Cited

U.S. PATENT DOCUMENTS

| | | | |
|---|---|---|---|
| 2010/0016719 A1 | 1/2010 | Freiburger et al. | |
| 2015/0148657 A1* | 5/2015 | Shashar | A61B 8/0875 600/440 |
| 2015/0305717 A1* | 10/2015 | Hollender | A61B 8/4494 600/438 |
| 2016/0128558 A1* | 5/2016 | Larin | A61B 3/0025 600/407 |
| 2018/0014814 A1* | 1/2018 | Labyed | A61B 8/485 |

OTHER PUBLICATIONS

Shi et al., Monitoring of radiofrequency ablation with shear wave delay mapping, 2015 IEEE International Ultrasonics Symposium (IUS), Oct. 21-24, 2015, 10.1109/ULTSYM.2015.0040 (Year: 2015).*
PCT/EP2019/061156 ISR & WO Jul. 24, 2019, 19 Page Document.

* cited by examiner

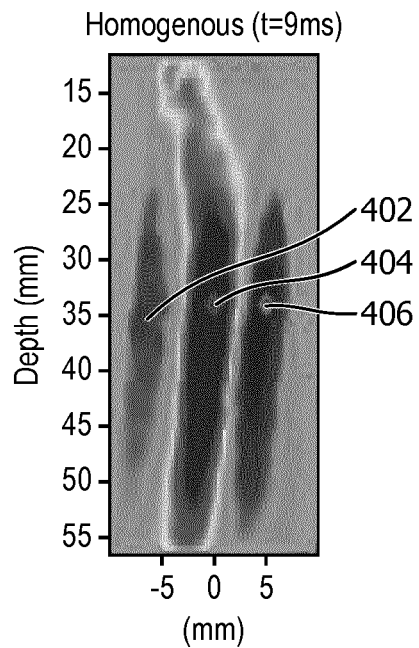
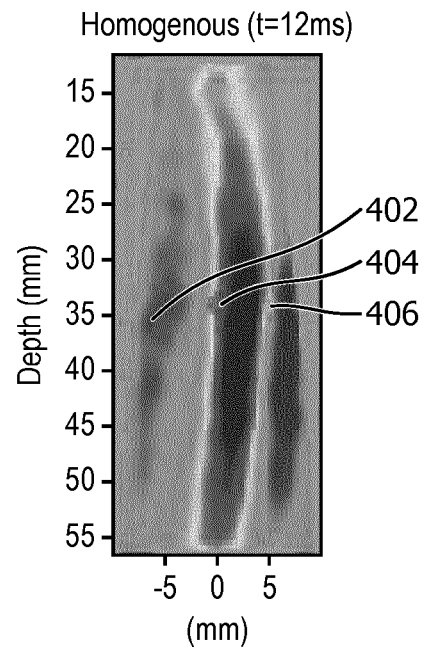
FIG. 4A
FIG. 4B
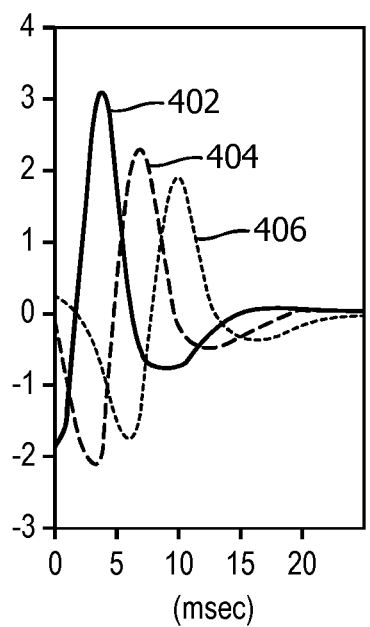
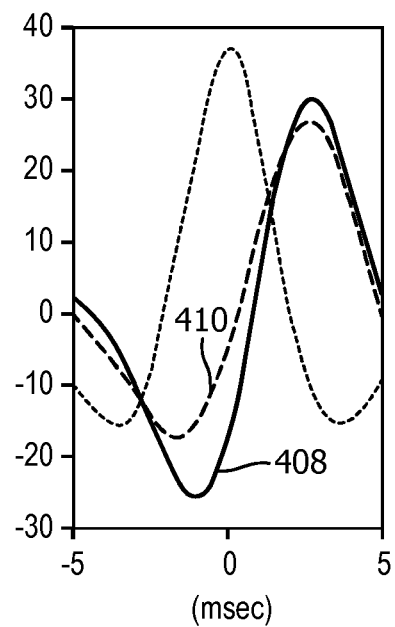
FIG. 4C
FIG. 4D

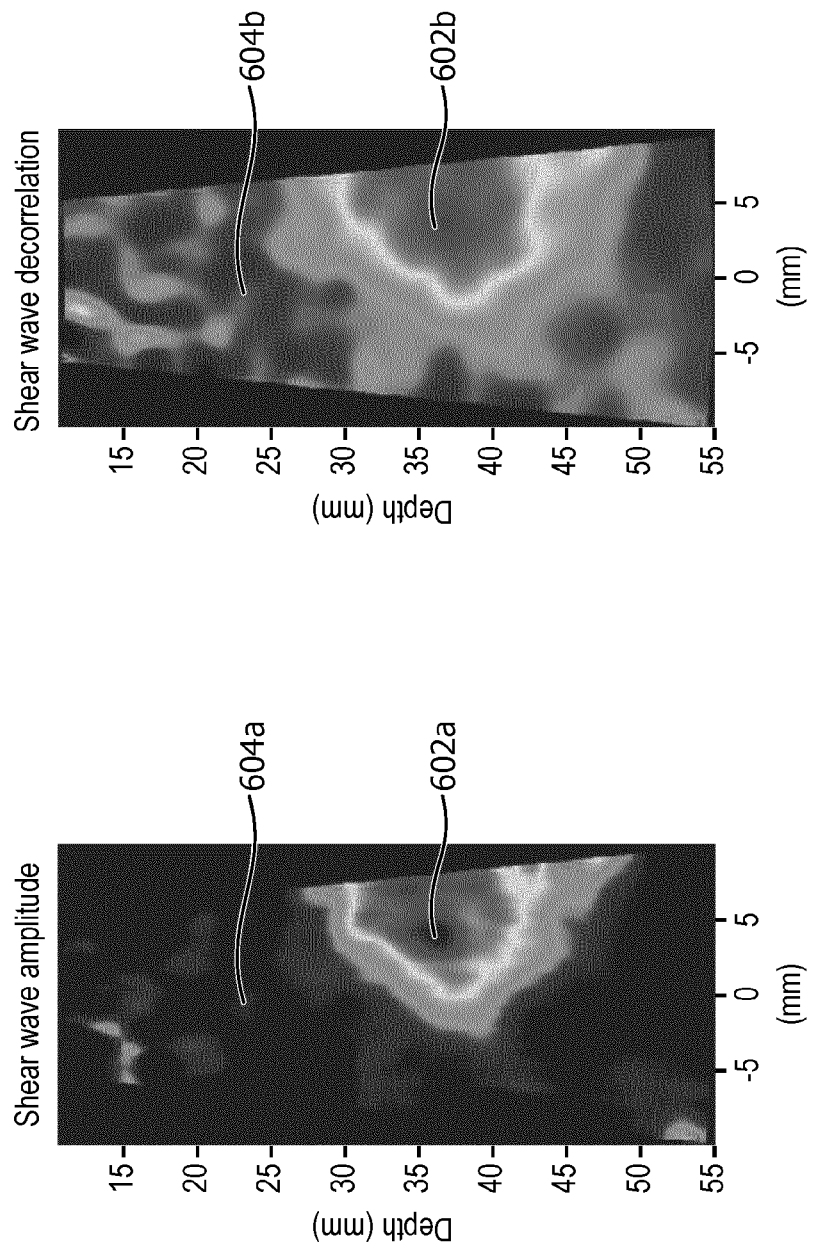

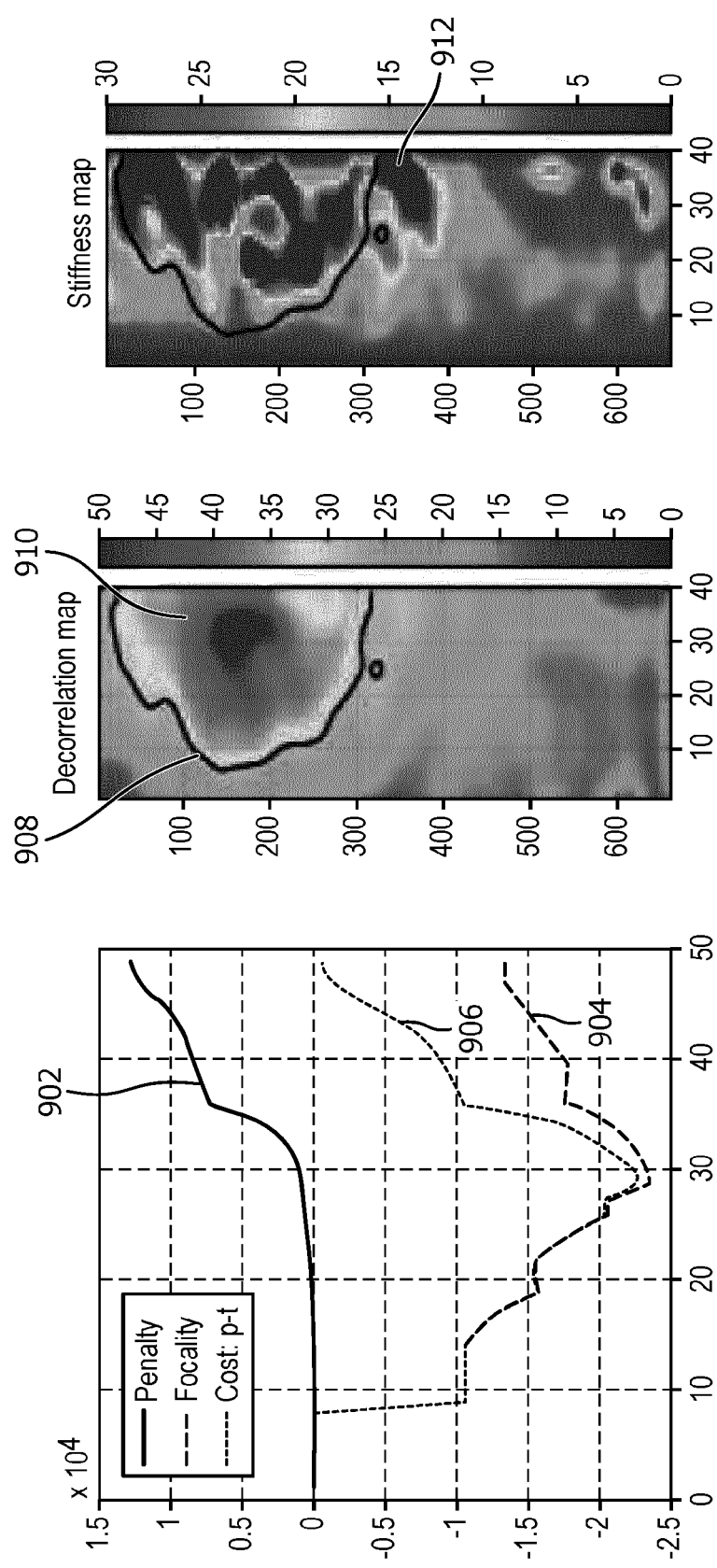
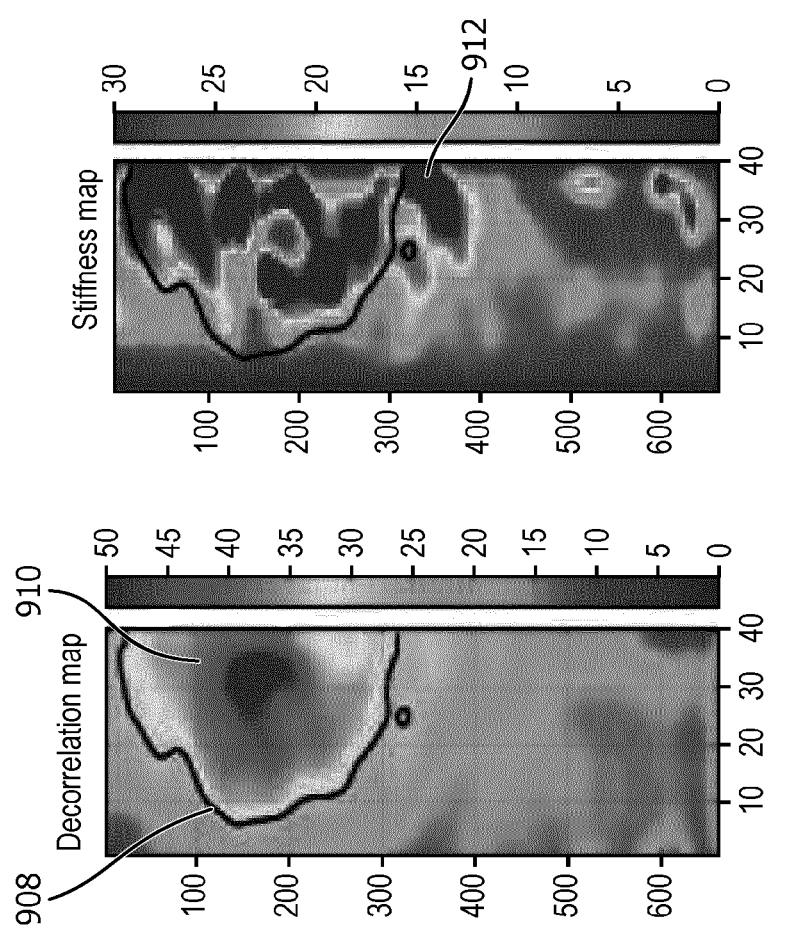
FIG. 9C
FIG. 9B
FIG. 9A

SHEAR WAVE AMPLITUDE RECONSTRUCTION FOR TISSUE ELASTICITY MONITORING AND DISPLAY

CROSS-REFERENCE TO PRIOR APPLICATIONS

This application is the U.S. National Phase application under 35 U.S.C. § 371 of International Application No. PCT/EP2019/061156, filed on May 1, 2019, which claims the benefit of U.S. Provisional Patent Application No. 62/741,905, filed on Oct. 5, 2018 and U.S. Provisional Patent Application No. 62/666,348, filed on May 3, 2018. These applications are hereby incorporated by reference herein.

TECHNICAL FIELD

The present disclosure pertains to ultrasound systems and methods for determining tissue elasticity. Particular implementations involve tissue elasticity determinations based on shear wave amplitude attenuation and decorrelation.

BACKGROUND

Radiofrequency ablation (RFA) is the most widely used form of curative treatment for liver cancer, which is currently the second leading cause of cancer death worldwide. RFA is minimally invasive, and involves heating tumors to the point of coagulation necrosis using an ablation electrode, needle, or tine inserted at the tumor site. Clear boundary delineation for tumors targeted by RFA is critical for targeting the cancerous tissue with precision. Current RFA treatment protocols often implement an ellipsoidal ablation volume prediction method; however, such methods are overly simplistic. As a result, the actual treatment volumes may deviate significantly from the predicted volumes, leading to off-target ablation of healthy tissue and/or incomplete ablation of tumor tissue.

Ultrasound imaging is commonly used for guidance during RFA procedures. Ultrasound shear wave elastography imaging (SWI), in particular, has been used to estimate the extent of ablation by measuring tissue elasticity. Ultrasound SWI can determine the localized stiffness levels of various tissues, including liver tissue, by transmitting a "push pulse" (phenomenon known as the acoustic radiation force) from a transducer into a tissue, thereby generating a shear wave that propagates laterally therethrough. Tracking pulses emitted by the transducer can then be used to measure the velocity of the shear wave as it propagates, which is often proportional to the stiffness of the tissue. For example, shear wave velocity in soft tissue is typically slower than shear wave velocity in stiff tissue, assuming an identical push pulse is used to generate the shear wave in each tissue type. Because ablated, necrotic tissue is usually much stiffer than untreated tissue, the boundaries of ablated tissue could theoretically be determined based on shear wave velocity; however, current SWI modalities and associated tissue reconstruction techniques are incapable of reliably deciphering such boundaries due to the high stiffness of thermal lesions created by RFA and the presence of a rigid ablation electrode at the treatment site. These factors reduce the amplitude of shear waves generated by SWI systems, increases the difficulty of detecting such waves amidst extraneous signals reflecting from various tissue features, thereby resulting in low signal-to-noise-ratios (SNRs) within an ablation zone. Elasticity estimates and quantitative elasticity maps of the ablation zones interrogated via SWI are thus widely inaccurate and unreliable. Improved tissue elasticity measurement and ablation monitoring techniques are needed to increase the precision of ablation therapies and tissue mapping.

SUMMARY

The present disclosure describes systems and methods for determining the elasticity of a target tissue via shear wave ultrasound imaging. The target tissue can include a region of increased stiffness, which may be localized and variable in size. In some examples, the region may comprise a thermal lesion created via an ablation procedure. While shear wave imaging has been utilized to determine tissue elasticity information in preexisting systems, such systems are often impeded by the low amplitude shear waves generated in regions of high stiffness, such as the stiff lesions created by thermal ablation. To accurately determine the location and boundaries of stiff tissue, systems herein are uniquely configured to determine the displacement amplitude of a propagating shear wave and based on this amplitude, derive a qualitative tissue elasticity map that indicates the location of the stiff region with accuracy and precision. To clearly demarcate the boundaries of the stiff region and improve computational efficiency, systems herein are also configured to remove noise from quantitative tissue maps of the same region. Specific examples include a processor configured to combine a qualitative tissue elasticity map with a quantitative tissue elasticity map, and based on the resulting combination, demarcate precise borders of the stiff region. In various embodiments, combining the two map types involves first generating a contour plot of tissue elasticity from the qualitative tissue elasticity map and then overlaying the contour plot onto the quantitative map. The contour line that best fits the region of increased stiffness is determined and selected.

In accordance with principles of the present disclosure, an ultrasound imaging system may include an ultrasound transducer configured to acquire echoes responsive to ultrasound pulses transmitted toward a target tissue. They system can also include a beamformer configured to transmit, from the ultrasound transducer, tracking pulses in response to a push pulse, wherein the push pulse generates a shear wave in the target tissue and the tracking pulses are spatially planned to intersect the shear wave at one or more locales. The beamformer can also receive, from the ultrasound transducer, echo signals where the tracking pulses intersected the shear wave. The system may also include a processor in communication with the beamformer and configured to store tracking echo data generated from the received echo signals; in response to the tracking echo data, determine a displacement amplitude of the shear wave propagating through the target tissue; and based on the determined displacement amplitude, generate a qualitative tissue elasticity map of the target tissue.

In some examples, the processor is configured to generate the qualitative tissue elasticity map by comparing the determined displacement amplitude to a reference displacement amplitude. In some embodiments, the determined displacement amplitude is determined at two or more laterally-spaced points within the target tissue, and the reference displacement amplitude is determined at two or more laterally-spaced points within a reference tissue or is determined numerically from a simulated model. In some embodiments, the reference tissue comprises a phantom model of the target tissue or a patient sample of a tissue type corresponding to the target tissue and lacking a region of increased stiffness.

In some examples, the processor is further configured to: determine a displacement amplitude decorrelation value by comparing the determined displacement amplitude at consecutive pairs of the laterally-spaced points within the target tissue; determine a reference displacement amplitude decorrelation value by comparing the determined displacement amplitude at consecutive pairs of the laterally-spaced points within the reference tissue; compare the displacement amplitude decorrelation value to the reference displacement amplitude decorrelation value; and based on the comparison, generate the qualitative tissue elasticity map. In some embodiments, the ultrasound transducer is coupled to an ablation device, the ablation device configured to ablate a region of increased stiffness or a larger region comprising the region of increased stiffness. In some examples, the ultrasound transducer, beamformer and processor are configured to operate concurrently with the ablation device. Example systems can further include a user interface configured to display the qualitative tissue elasticity map. In some embodiments, the reference displacement amplitude is derived from a reference map. In some examples, the system also includes a memory configured to store a plurality of reference maps. In some embodiments, the target tissue comprises a region of increased stiffness comprised of a thermal lesion.

In accordance with principles of the present disclosure, an ultrasound imaging system for shear wave imaging includes an ultrasound transducer configured to acquire echoes responsive to ultrasound pulses transmitted toward a target tissue. The system may also include a beamformer configured to: transmit, from the ultrasound transducer, tracking pulses in response to a push pulse, wherein the push pulse generates a shear wave in the target tissue and the tracking pulses are spatially planned to intersect the shear wave at one or more locales; and receive, from the ultrasound transducer, echo signals where the tracking pulses intersected the shear wave. The system can also include a processor in communication with the beamformer. The processor can be configured to: generate a qualitative tissue elasticity map of the target tissue based on the received echo signals; generate a quantitative tissue elasticity map of the target tissue based on the received echo signals; and determine a boundary of a region of increased stiffness within the target tissue by combining the qualitative tissue elasticity map with the quantitative tissue elasticity map.

In some examples, the processor is further configured to derive a contour plot demarcating regions of uniform stiffness from the qualitative tissue elasticity map. In some embodiments, combining the qualitative tissue elasticity map with the quantitative tissue elasticity map comprises overlaying the contour plot onto the quantitative tissue elasticity map. In some embodiments, the processor is configured to determine the boundary of the region of increased stiffness by further determining a contour line of best fit around the region of increased stiffness. In some implementations, the contour line of best of is selected from two or more candidate contour lines of best fit based on a set of criteria selectable by a user. In some examples, the set of criteria comprises an over-inclusiveness bias, such that the contour line of best fit comprises the contour line that defines a greatest area of tissue. In some embodiments, the processor is further configured to generate a hybrid tissue elasticity map based on the determined boundary of the region of increased stiffness. In some embodiments, the processor is configured to generate the hybrid map by masking at least one area of the hybrid map outside of the determined boundary. Example systems can further include a user interface configured to display the hybrid map. In some implementations, the quantitative tissue elasticity map comprises a tissue elasticity gradient map. In some embodiments, the processor is configured to determine the contour line of best fit by: summing gradient values along each contour line within the contour plot; dividing a sum of gradient values for each contour line by a length of each contour line; and selecting a contour line with a maximum average gradient. In some examples, the ultrasound transducer is coupled to an ablation device, the ablation device configured to ablate the region of increased stiffness or a larger region comprising the region of increased stiffness. In some embodiments, the region of increased stiffness comprises a thermal lesion.

In accordance with principles of the present disclosure, a method of shear wave imaging may involve acquiring ultrasound echoes responsive to ultrasound pulses transmitted toward a target tissue; transmitting a push pulse into the target tissue to generate a shear wave in the target tissue; transmitting tracking pulses spatially planned to intersect the shear wave at one or more locales; receiving echo signals where the tracking pulses intersected the shear wave; storing tracking echo data generated from the received echo signals; determining a displacement amplitude of the shear wave propagating through the target tissue based on the tracking echo data; and generating a qualitative tissue elasticity map of the target tissue based on the determined displacement amplitude.

In some examples, generating the qualitative tissue elasticity map of the target tissue based on the determined displacement amplitude comprises comparing the determined displacement amplitude to a reference displacement amplitude. In some embodiments, the determined displacement amplitude is determined at two or more laterally-spaced points within the target tissue, and the reference displacement amplitude is determined at two or more laterally-spaced points within a reference tissue or is determined numerically from a simulated model. In some examples, the method further involves determining a displacement amplitude decorrelation value by comparing the determined displacement amplitude at consecutive pairs of the laterally-spaced points within the target tissue; determining a reference displacement amplitude decorrelation value by comparing the determined displacement amplitude at consecutive pairs of the laterally-spaced points within the reference tissue; comparing the displacement amplitude decorrelation value to the reference displacement amplitude decorrelation value; and based on the comparison, generating the qualitative tissue elasticity map.

In some embodiments, the method further involves displaying the qualitative tissue elasticity map on a user interface. In some examples, the reference displacement amplitude is derived from a reference map. In some embodiments, the target tissue comprises a region of increased stiffness comprised of a thermal lesion.

In accordance with principles of the present disclosure, a method of shear wave imaging may involve: acquiring ultrasound echoes responsive to ultrasound pulses transmitted toward a target tissue; transmitting a push pulse into the target tissue to generate a shear wave in the target tissue; transmitting tracking pulses spatially planned to intersect the shear wave at one or more locales; receiving echo signals where the tracking pulses intersected the shear wave; storing tracking echo data generated from the received echo signals; generating a qualitative tissue elasticity map of the target tissue based on the received echo signals; generating a quantitative tissue elasticity map of the target tissue based on the received echo signals; and determining a boundary of a region of increased stiffness within the target tissue by combining the qualitative tissue elasticity map with the quantitative tissue elasticity map.

In some examples, the method further involves deriving a contour plot demarcating regions of uniform stiffness from the qualitative tissue elasticity map. In some embodiments, combining the qualitative tissue elasticity map with the quantitative tissue elasticity map comprises overlaying the contour plot onto the quantitative tissue elasticity map. In some examples, determining the boundary of the region of increased stiffness comprises determining a contour line of best fit around the region of increased stiffness. In some embodiments, generating a hybrid tissue elasticity map based on the determined boundary of the region of increased stiffness by masking at least one area outside of the determined boundary. In some examples, the region of increased stiffness comprises a thermal lesion.

Any of the methods described herein, or steps thereof, may be embodied in non-transitory computer-readable medium comprising executable instructions, which when executed may cause a processor of a medical imaging system to perform the method or steps embodied herein.

BRIEF DESCRIPTION OF THE DRAWINGS

FIG. 4A is a reference shear wave amplitude displacement map constructed at a first timepoint in accordance with principles of the present disclosure.

FIG. 4B is a reference shear wave amplitude displacement map constructed at a second timepoint in accordance with principles of the present disclosure.

FIG. 4C is a reference shear wave amplitude displacement graph constructed in accordance with principles of the present disclosure.

FIG. 4D is a reference shear wave decorrelation graph constructed in accordance with principles of the present disclosure.

FIG. 6A is a shear wave displacement amplitude reconstruction map constructed in accordance with principles of the present disclosure.

FIG. 6B is a shear wave decorrelation reconstruction map constructed in accordance with principles of the present disclosure.

FIG. 9A is a graph of best fit metrics applied to candidate contour lines demarcating a lesion according to principles of the present disclosure.

FIG. 9B is a shear wave decorrelation reconstruction map overlaid with an optimum contour line identified in the graph of FIG. 9A.

FIG. 9C is a quantitative elasticity map overlaid with the optimum contour line shown in FIG. 9B.

DETAILED DESCRIPTION

Figure 1:
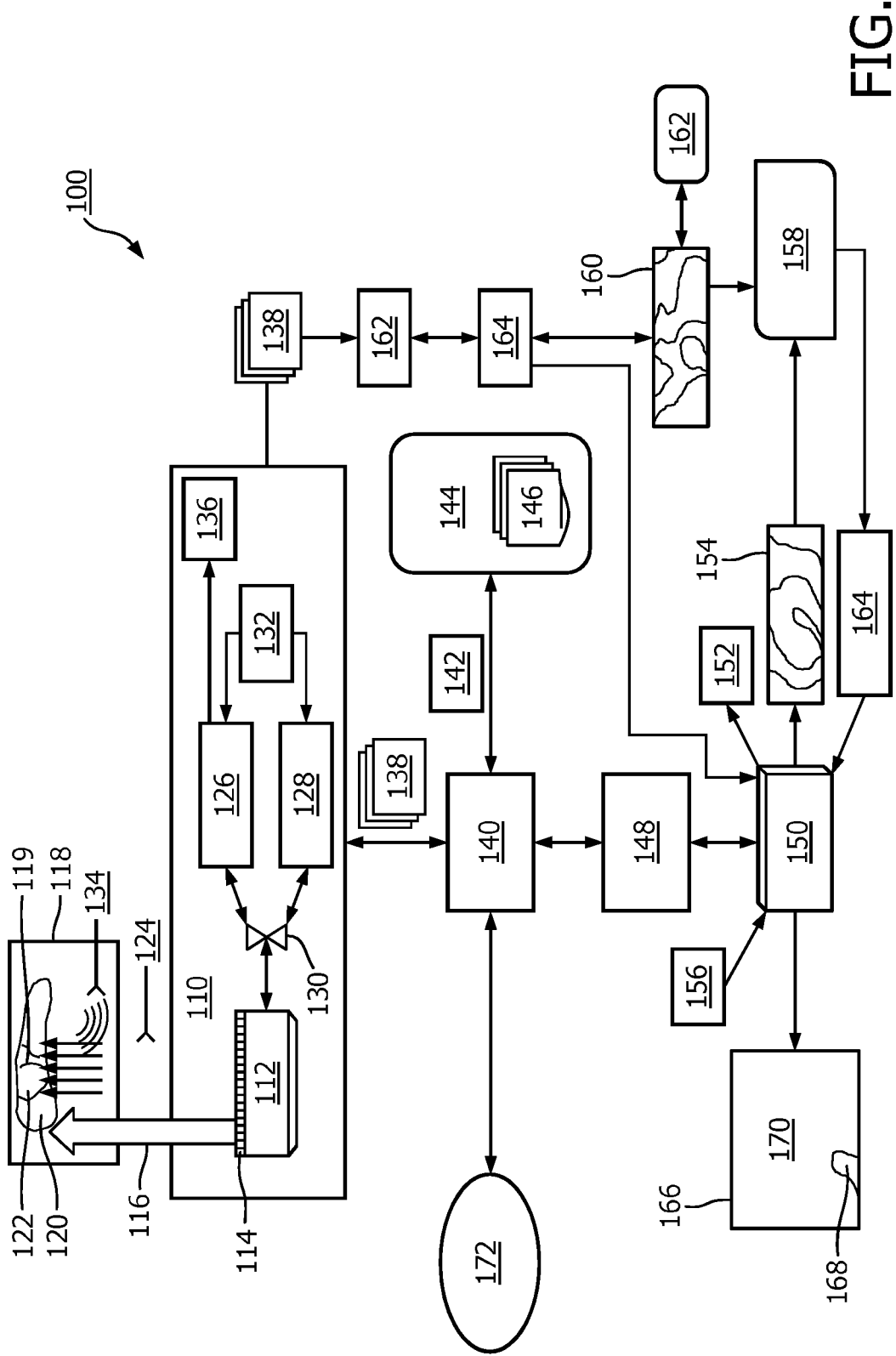
FIG. 1 is a block diagram of an ultrasound imaging system constructed in accordance with principles of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Provided herein are ultrasound-based SWI systems configured to provide accurate, real-time monitoring and display of tissue ablation in a manner that improves the precision of the ablation procedure. Preexisting ablation monitoring systems may utilize SWI to estimate tissue elasticity by measuring the propagation speed of shear waves passing through a region of tissue. Such time-of-flight approaches, also referred to as time-to-peak reconstructions, typically estimate shear wave speed by measuring wave delays detected across the region via laterally spaced tracking beams emitted from an ultrasound transducer. Multiple factors associated with RFA diminish the accuracy of such techniques. For example, time-of-flight approaches are hindered by low signal-to-noise ratios due to the low amplitude of shear waves passing through RFA-generated thermal lesions, which may be 6-8 times stiffer than surrounding tissue, healthy or cancerous, due to the tissue's desiccated state after ablation. Shear waves travel quickly through such stiff tissue, causing a reduction in the amplitude of the waves. As an ablation procedure continues, the volume of the thermal lesion grows, as does the proportion of unreliable quantitative data produced by low-amplitude shear waves, such that near then end of the procedure, when the smallest amount of tumor tissue remains, the accuracy of ablation monitoring may be the lowest. The precision of continued ablation may thus reach a low point at the most critical point in the procedure, i.e., when the least amount of cancerous tissue remains, thereby amplifying the risk of off-target ablation of healthy tissue and incomplete ablation of cancerous tissue. SW elastography assumes free field shear wave propagation and the presence of a solid ablation electrode, or tine, utilized in RFA invalidates this assumption and may further reduce the amplitude of propagating shear waves, even if the electrode is not placed directly within the shear wave imaging field-of-view. The cumulative effect of these factors is a consistently low SNR, which prevents the elucidation of tissue elasticity maps of even moderate resolution or accuracy. To resolve these issues, systems disclosed herein improve ultrasound SWI by discerning lesion boundaries with high sensitivity, even in close proximity to a rigid ablation needle, and providing comprehensive, real-time ablation monitoring and display over an entire ablation zone. Example systems can be specifically configured to generate qualitative tissue elasticity maps by detecting shear wave amplitude displacements and correlation values at different spatial locations within a treatment site. Systems are also configured to combine quantitative tissue elasticity maps with qualitative tissue reconstruction maps in a manner that enhances the accuracy of lesion boundary delineation. While most of the examples described herein are related to determining the location and boundaries of tissue lesions created via ablation, one skilled in the art should understand that the disclosed systems can be utilized to interrogate many tissue types, including regions of stiff tissue, whether or not a lesion is present, and regions of tissue producing low amplitude shear waves in response to receiving a push pulse.

FIG. 1 shows an example ultrasound system 100 configured to perform shear wave elastography across an ablation zone, determine the boundaries of the ablation zone by producing accurate tissue elasticity data, and generate qualitative elasticity maps of the ablation zone based on the data produced. The system 100 can include an ultrasound acquisition unit 110, which can include an ultrasound probe 112 housing an ultrasound sensor array 114 configured to transmit and receive ultrasound signals. The array 114 is configured to emit a high-amplitude push pulse 116 into a target region 118, which may contain one or more tissue abnormalities 120, such as a tumor or stiff tissue inclusion. In additional or alternative embodiments, the push pulse 116 may be generated by an array other than the array 114. For instance, in some examples, one array may be used for applying the acoustic radiation force (ARF) and a different array may be used for imaging. In yet other examples, the tissue may be stimulated mechanically, for example using an external mechanical actuator configured to apply an external mechanical force. Depending on the treatment stage, at least one ablation zone 122, which may also be referred to as a coagulation zone or thermal lesion, may also be present. The target region 118 may comprise an organ, including but not limited to a human liver, pancreas, kidney, lung, heart, or brain, or an area of tissue, e.g., muscle tissue. The array 114 is also configured to transmit a plurality of tracking pulses or beams 124 into the target zone 118 to detect propagation of the shear wave 119 created by the push pulse 116. The tracking pulses 124 can be transmitted adjacent to the push pulse 116 and in some examples may be laterally-spaced with respect to the push pulse. In some embodiments, the tracking pulses 124 can be parallel to the push pulse 116, for example, when a linear probe is utilized to emit the tracking pulses. In other examples, the tracking pulses 124 may not be transmitted parallel to the push pulse 116. For instance, a curved probe may transmit tracking pulses in a radial direction with angular separation therebetween. Such pulses may not be parallel in the Cartesian space, but they are transmitted in the same direction in the polar or cylindrical coordinate frames. The array 114 is coupled to a transmit beamformer 126 and a multiline receive beamformer 128 via a transmit/receive (T/R) switch 130. Coordination of transmission and reception by the beamformers 126, 128 can be controlled by a beamformer controller 132. In operation, the transmit beamformer 126 may control the array 114 to transmit one or more, e.g., a series, of push pulses 116 into the target region 118, adjacent to the ablation zone 122, which may comprise an anticipated ablation zone if an ablation procedure has not yet commenced. The multiline receive beamformer 128 can produce spatially distinct receive lines (A-lines) of echo signals 134, which can be received by the array 114 and processed by filtering, noise reduction, etc. by a signal processor 136. In some embodiments, the components of the acquisition unit 110 may be configured to generate a plurality of sequential ultrasound image frames 138 from the ultrasound echoes 134.

The system 100 may also include one or more processors, such as a qualitative processing module 140, which can be configured to determine the displacement amplitude of the shear wave 119 propagating through the ablation zone 122. In embodiments, the displacement amplitude can be detected at two or more laterally-spaced points within the ablation zone 122, such that attenuation of the displacement amplitude across the tissue, away from the push pulse, can be determined. The qualitative processing module 140 can then compare the amplitude attenuation to a reference amplitude attenuation derived from a selected reference map 142. As shown in FIG. 1, the reference map 142 can be selectively extracted from a memory component 144 communicatively coupled with the qualitative processing module 140. The memory component 144 may store a plurality of reference maps in a library or database 146. Based on the comparison between the determined amplitude attenuation and the reference amplitude attenuation, the qualitative processing module 140 can reconstruct the elasticity of the underlying tissue within and near the ablation zone 122 with high precision despite the low amplitude of the shear wave 119 generated by the push pulse 116.

In various embodiments, the system 100 also includes a display processor 148 coupled with the qualitative processing module 140, along with a user interface 150 configured to display the outputs of the display processor. The display processor 148 can be configured to generate ultrasound images 152 from the image frames 138 and a qualitative shear wave reconstruction map 154. As described below, the qualitative shear wave reconstruction map 154 may comprise a shear wave displacement amplitude reconstruction map or a shear wave decorrelation reconstruction map, which both may embody qualitative representations of tissue elasticity within and near a tissue ablation zone. The user interface 150 can be configured to display the images 152 and qualitative reconstruction map 154 in real time as an ultrasound scan and/or ablation procedure is being performed, and may receive user input 156 at any time before, during or after such procedures. In some examples, the ultrasound images and/or maps displayed on the user interface 150 can be updated at every acquisition frame received and processed by the data acquisition unit 110 during an ultrasound SWI scan and, in some embodiments, during an ablation procedure.

In some implementations, the system 100 also includes a boundary module 158 configured to receive the qualitative shear wave reconstruction map 154 and a quantitative elasticity map 160, and based on the two maps, refine the determined boundaries of a lesion, which may comprise a thermal lesion created via ablation, or a region of stiff tissue. For simplicity, lesion boundaries are referred to herein, although it should be understood to one skilled in the art that additional tissue boundaries, e.g., organ boundaries or localized areas of increased stiffness such as some cancerous lesions, are also discernable via the systems and methods disclosed. By refining the boundaries of the lesion, the boundary module 158 may reduce or eliminate signaling noise previously blurring the boundaries of the lesion, thereby increasing the accuracy and precision of the system 100. The boundary module 158 may be configured specifically to determine an absolute threshold that precisely tracks the actual, physical boundaries of a lesion. The quantitative elasticity map 160 may be generated from the ultrasound image frames 138 generated by the data acquisition unit 110 during SWI. In specific embodiments, a quantitative processing module 162 may generate the quantitative elasticity map 160 from the image frames 138. The quantitative stiffness maps can be stored in a memory component 162. As further shown, a boundary display processor 164, which may be coupled with the user interface 150, can also be included. The display processor 164 can be configured, either alone or with the boundary module 158 and/or user interface 150, to generate a hybrid map 166 that includes a lesion 168 and at least one masked area 170 outside the lesion boundaries.

The configuration of the system 100 shown in FIG. 1 may vary. For example, the system 100 can be portable or stationary. Various portable devices, e.g., laptops, tablets, smart phones, or the like, may be used to implement one or more functions of the system 100. In examples that incorporate such devices, the ultrasound sensor array 114 may be connectable via a USB interface, for example. The system 100 can operate concurrently with an ablation device 172 configured to perform an ablation therapy comprising but not limited to: RFA, microwave ablation, or high-intensity focused ultrasound ablation. In some examples, the ablation device 172 can include a needle, tine or probe configured to be inserted into the tissue constituting the ablation zone 122, where the device directs localized heat in some embodiments. One or more components of the system 100 may be communicatively, operatively and/or physically coupled with the ablation device 172, such that the device and the system may be responsive to the operation of the other. For example, in some embodiments the ablation device 172 may be configured to adjust the size and/or location of an ablation zone based on a tissue elasticity map generated by the qualitative processing module 140 and/or boundary module 158. The system 100 may thus improve ablation accuracy and/or reduce ablation time by providing the ablation device 172 and/or its operator with information regarding the location and/or boundaries of a lesion during or prior to an ablation procedure. In some examples, the system 100 can also be configured to operate in tandem with an image-guided biopsy procedure, during which the effective stiffness of the biopsy target is often increased due to the presence of a biopsy needle. The system 100 may also be employed to determine tissue elasticity in tissues that cause strong shear wave attenuation, such as lesions that may occur as a result of disease, e.g., fatty liver disease. Such tissues may not harbor any ablated regions or needles. One or more components shown in FIG. 1 may be combined in some examples. For instance, the qualitative processing module 140, quantitative processing module 162 and/or boundary module 158 may be combined into one processing module in some embodiments. The quantitative and qualitative display processors 164, 148 may also be integrated in some examples.

The reference maps 142 can be derived from various sources. In some examples, the reference maps 146 can be derived from artificially created tissue phantoms, which can be designed to mimic specific tissue types and may harbor one or more areas of increased stiffness to mimic the existence of lesions within the tissue. For example, reference maps 142 may be created for liver phantoms, bladder phantoms, lung phantoms, etc., which may harbor one or more tumors and/or ablated areas. In addition or alternatively, the reference maps 142 can be derived from actual patient tissues. The tissues used to create the reference maps 146 can be healthy tissue, e.g., elastically homogenous tissue lacking any lesions, tumors or other abnormalities. The SNR ratios obtained from such tissues may be higher than heterogeneous tissue, thus making the tissues more reliable as a baseline reference. In some examples, however, tissue that does harbor at least one abnormality may be utilized as a reference. For example, in some embodiments the reference map 142 may be a map of cancerous tissue derived from a patient subjected to ultrasound SWI at an earlier time point. By comparing amplitude attenuation values for the same tissue obtained at different time points, the expansion or reduction in abnormal tissue, and thus treatment progress, can be determined. Progress can be tracked across treatments, or after individual treatments. For instance, a reference map may be created before an ablation procedure, written to the memory 144, and then read from the memory for comparative purposes one or more times during or immediately following the procedure. The reference maps 142 can be modified over time, as new data is accrued, or simply replaced each time a new ultrasound scan is performed. In addition or alternatively, the reference maps 142 can be derived from numerical models, e.g., simulated, numerically-calculated models. Quantitative SWI measurements may or may not be used to modify the model properties. In some examples, reference tissue information may not be derived from a tissue sample or numerical model, and may instead be derived from a priori knowledge of a particular medium. In some implementations, reference maps 142 can be created for a variety of tissues, such that the amplitude attenuation determined for a specific tissue type, e.g., liver tissue, can be compared to amplitude attenuation values determined from a reference map derived from the same tissue type. Reference maps 142 can be created and stored in memory 144 each time SWI is performed using the system 100, such that a library of reference maps 146 can be supplemented over time. Comprehensive libraries may contain reference maps specific to multiple patients and/or tissue types.

The qualitative processing module 140 can be configured to selectively extract a specific reference map 142 based on one or more factors. For example, the qualitative processing module may be configured to select a reference map that corresponds to the tissue type being currently examined and/or targeted for ablation. The processing module may also be configured to select a reference map that corresponds to the specific patient being currently examined. Reference maps derived from the same patient can be stored over time, and the processing module can be configured to select reference maps stored at specific time points. In some embodiments, a user can manually select a particular reference map. In addition or alternatively, the qualitative processing module can select a particular reference map automatically, without user input. According to such examples, the qualitative processing module may be configured to apply reference map selection criteria. For example, the qualitative processing module may prioritize patient identity over tissue type, such that the module first requests a reference map corresponding to a particular patient being currently examined. If no reference maps are available for that particular patient, the module may proceed to request a reference map corresponding to the particular tissue type being examined, regardless of patient identity. Additional criteria, such as patient age and/or health, may also be applied by the processing module to cull specific maps from the memory during an ultrasound scan and/or tissue ablation procedure.

Figure 2:
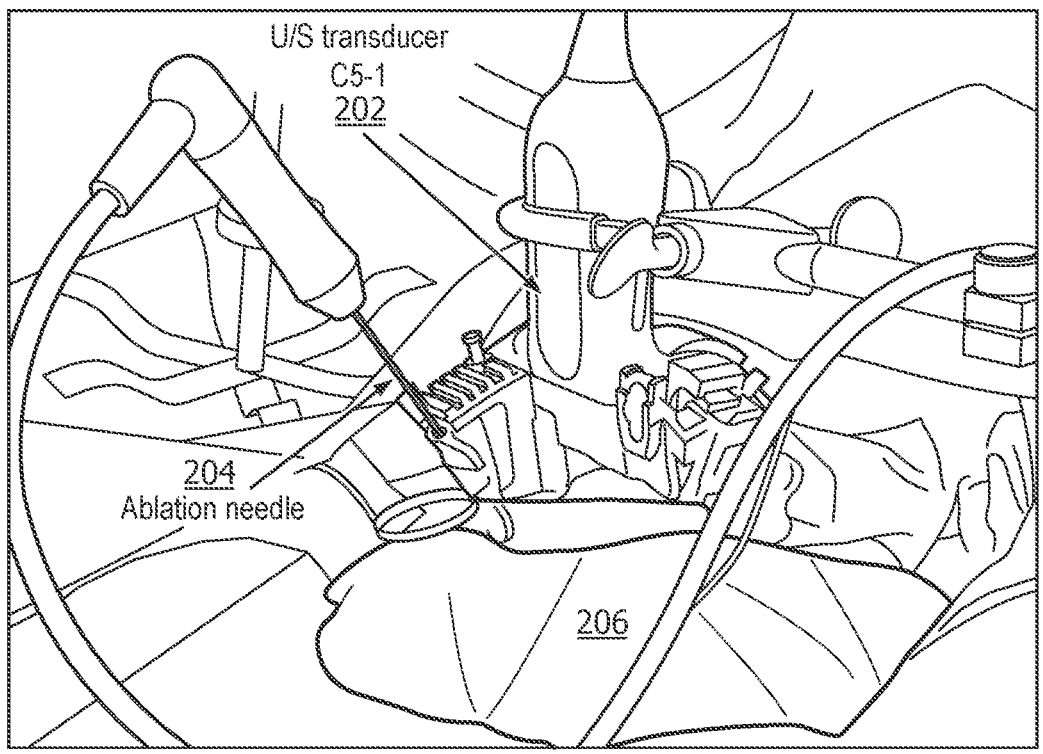
FIG. 2 is a photograph of an ultrasound shear wave imaging system operating concurrently with a tissue ablation system in accordance with principles of the present disclosure.

FIG. 2 is a photograph of an ultrasound system operating concurrently with an ablation system. An ultrasound transducer 202 and ablation needle 204 are aimed at a region of interest within a liver 206. The ultrasound transducer 202 can be configured to emit push pulses into an area of the liver 206 adjacent to the ablation site targeted by the ablation needle 204. As shown, the imaging components and ablation components may be physically coupled in close proximity, such that imaging and ablation can be performed on the same tissue region at the same time. The tissue shown in FIG. 2 is liver tissue, but one skilled in the art should understand that the systems and methods described herein are not limited to liver, and can be applied to a wide range of tissue types.

Figure 3:
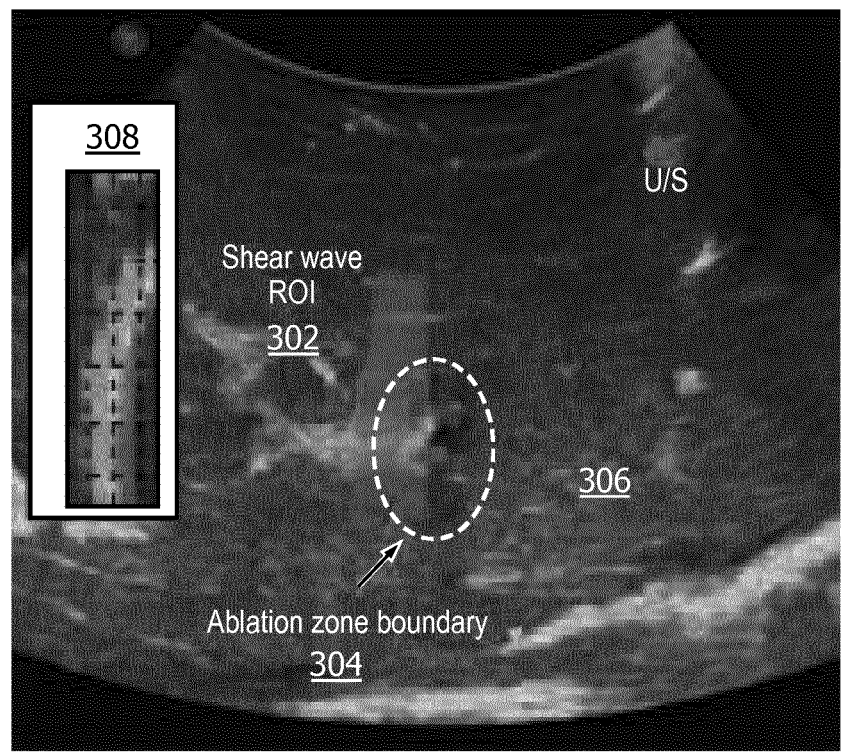
FIG. 3 is an ultrasound image and corresponding tissue elasticity map of an ablation zone and adjacent region of interest generated by the systems shown in FIG. 2.

FIG. 3 is an ultrasound image of the tissue region obtained by the ultrasound SWI system shown in FIG. 2. A shear wave region of interest 302 is indicated, along with an ablation zone boundary 304 and an ablation needle target site 306. An elasticity map 308 of the shear wave ROI is overlaid onto the image. The shear wave ROI 302 encompasses the region of tissue through which the shear wave propagates after emission of each push pulse into the tissue (top to bottom in this image), and can be positioned adjacent the ablation needle target site 306 and overlapping with the ablation zone boundary 304. To detect displacement amplitudes of the propagating shear wave, laterally-spaced tracking beams can be emitted into the shear wave ROI 302. As shown, the push beam can be transmitted into the tissue just outside of the anticipated lesion area. Thus, the system is configured to determine the tissue elasticity properties of a region that has different elastic properties than an adjoining, e.g., ablated, region.

In various embodiments, one or more of the zones shown in FIG. 3 may be automatically defined by the ultrasound SWI system, either alone or in cooperation with the ablation system. In some examples, a user operating the system can modify, e.g., reposition and/or resize, the shear wave ROI 302, the ablation zone boundary 304 and/or the target site of the ablation needle 306. Such modifications may be input at a user interface displaying the ultrasound image. In some embodiments, the spatial relationship between two or more zones may be predefined, such that adjustment of one zone spurs automatic adjustment of another zone. For example, adjustment of the ablation zone boundary 304 may cause adjustment of the shear wave ROI 302, and vice versa. In addition or alternatively, the ablation needle target site 306 can be specified at a user interface, e.g., user interface 150, for example by moving a graphic representing the needle on the screen. The shear wave ROI 302 and ablation zone boundary 304 may move automatically in response to movement of the needle target site 306 to maintain a consistent spatial arrangement between the ablation zone and the imaged area. The coverage area imaged by the ultrasound transducer may vary, ranging from about 1 to about 10 cm, about 2 to about 8 cm, about 3 to about 6 cm, about 4 to about 5 cm, or about 2 to about 3 cm wide. In various embodiments, the tissue maps generated by systems herein may span the entire coverage area. As the shear waves propagate through the shear wave ROI 302, wave amplitude may decrease. Variation in the underlying tissue properties, such as the presence of a stiff ablated region within the ablation zone boundary 304, may cause additional changes in the wave amplitude, changing the attenuation pattern of the waves. Any changes in the underlying material properties of the tissue, such as increases in stiffness caused by thermal ablation, will cause changes in the attenuation of shear wave amplitude. Systems herein are configured to detect such variation by comparing shear wave displacement amplitudes to reference displacement amplitudes. For example, by determining peak-to-peak differences between a current shear wave amplitude and a reference shear wave amplitude at laterally spaced points within a target region, attenuation variation can be detected by the qualitative processing module 140.

FIGS. 4A and 4B illustrate reference amplitude displacement maps of shear wave propagation through a ROI within a homogenous tissue medium, which may comprise a lesionless medium, real or artificial, characterized by approximately consistent elasticity. The displacement maps can be generated by the qualitative processing module 140 operating cooperatively with the data acquisition and display components shown in FIG. 1. After generation of the reference maps, they can be stored within the memory component 144 and later extracted by the qualitative processing module in response to initiation of an ultrasound SWI procedure. FIG. 4A provides a snapshot of the shear wave propagation nine milliseconds after transmission of a push pulse, and FIG. 4B provides a snapshot of the shear wave propagation 12 milliseconds after transmission of the push pulse. Tissue depth is indicated on the y-axis, and lateral distance within the tissue indicated on the x-axis. Three laterally-spaced points 402, 404, 406 are indicated on each map. The coordinates of each point can be specified automatically, e.g., by a processing module. In some examples, coordinates can be specified manually, e.g., via receipt of user input, but in some examples, only a ROI is specified by a user. The specific placement and number of the points shown in each figure are for illustration purposes only, and should not be viewed as limiting. The points are specified pursuant to determining elasticity information eventually embodied in a reconstruction map. FIG. 4C is a graph of shear wave displacement profiles detected at each of the points 402, 404, 406, measured over time, and FIG. 4D is a graph of the corresponding cross-correlation values between consecutive pairs of the laterally-spaced points. As is evident in FIG. 4C, the maximum absolute shear wave displacement was detected at the first point 402, which is positioned nearest the site of the push pulse, about 3 milliseconds after transmission thereof.

Figure 5A:
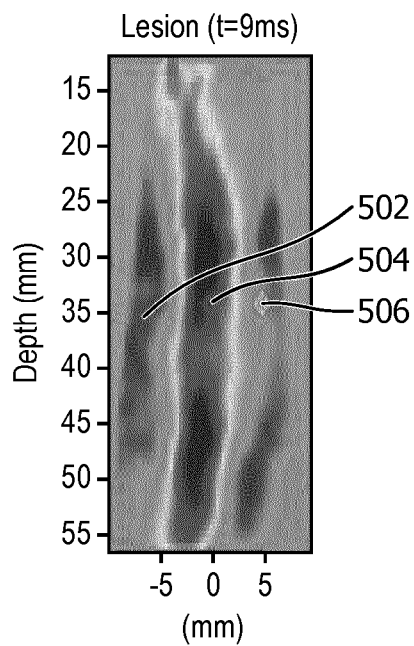
FIG. 5A is a shear wave amplitude displacement map constructed at a first timepoint in accordance with principles of the present disclosure.
Figure 5B:
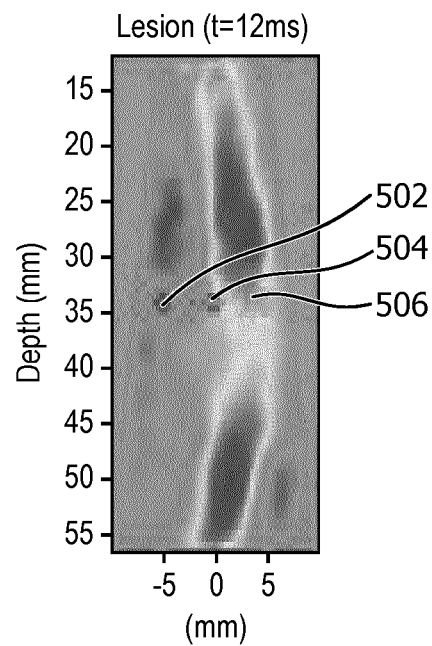
FIG. 5B is a shear wave amplitude displacement map constructed at a second timepoint in accordance with principles of the present disclosure.
Figure 5C:
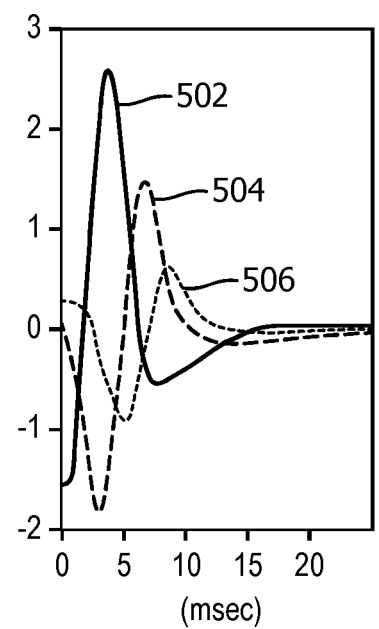
FIG. 5C is a shear wave amplitude displacement graph constructed in accordance with principles of the present disclosure.
Figure 5D:
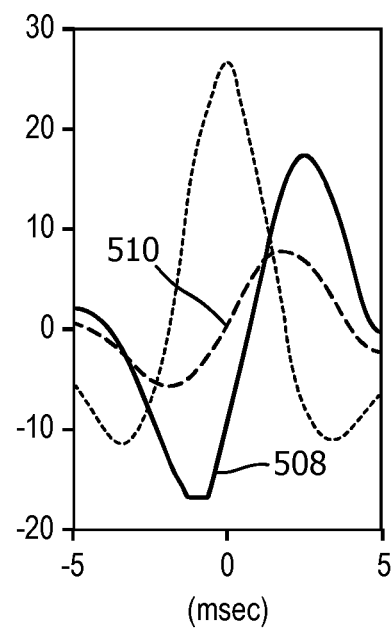
FIG. 5D is a shear wave decorrelation graph constructed in accordance with principles of the present disclosure.

FIGS. 5A and 5B illustrate amplitude displacement maps of shear wave propagation through a ROI within a heterogeneous medium, which may comprise at least one lesion, and is characterized by different elasticity value compared to the rest of the medium. The amplitude displacement maps can be generated by the qualitative processing module 140 during ultrasound SWI and an ablation procedure using the components of FIG. 1. As described herein, the displacement amplitude maps can be compared to the reference amplitude displacement maps to identify variations in shear wave attenuation between the maps. FIG. 5A provides a snapshot of the shear wave propagation nine milliseconds after transmission of a push pulse, and FIG. 5B provides a snapshot of the shear wave propagation 12 milliseconds after push pulse transmission. Three laterally-spaced points 502, 504, 506 are indicated on each map. Like the points shown in FIG. 4B, the points indicated in FIG. 5B can be specified automatically or in some examples, manually. As above, the points shown in FIG. 5B are for illustration purposes only, and should not be viewed as limiting. FIG. 5C is a graph of shear wave displacement profiles detected at each of the points 502, 504, 506, measured over time, and FIG. 5D is a graph of the corresponding cross-correlation values between consecutive pairs of the laterally-spaced points.

A qualitative shear wave amplitude displacement reconstruction map can be calculated from the displacement profiles shown in FIGS. 4C and 5C, either by determining the maximum amplitude displacement at each point 502, 504, 506 ("peak displacement"), or by determining the difference between the maximum and minimum at each point 502, 504, 506 ("peak-to-peak displacement"), and comparing such values to the corresponding peak displacements or peak-to-peak displacements determined at each reference point 402, 404, 406. For instance, the displacement amplitude value of a single pixel located at $x_0, y_0$ can be given as $p(x_0,y_0)=D(x_0,y_0)/D_{ref}(x_0,y_0)$, where D represents the displacement peak amplitude or peak-to-peak amplitude, and ref indicates a corresponding amplitude value extracted from a selected reference map. Shear wave displacement amplitude can be detected for each received ultrasound beam. The number of receive beams can vary, ranging from about 40 to about 48 in some embodiments. Along each receive beam, the displacement amplitude can be determined at a high resolution along the vertical axis, e.g., at each of about 300 to about 600 pixels. The number of points in the vertical axis is reduced at the scan conversion step later on before displaying the maps. The qualitative map 154 can be obtained, in some examples, by performing a peak or peak-to-peak analysis of the shear wave amplitude for each spatially distinct A-lines received at the data acquisition unit 110.

In some examples, systems herein can also be configured to generate a shear wave decorrelation map, which embodies the correlation between shear wave amplitude displacement profiles at two laterally-spaced points. By comparing the correlation values between laterally-spaced points to correlation values derived from comparable laterally-spaced points in a reference map, variations in shear wave correlation, and thus tissue elasticity, can be identified. In some embodiments, decorrelation maps may be preferred over shear wave amplitude displacement maps because decorrelation maps can also be sensitive to changes in wave shape and frequency. Line 408 in FIG. 4D represents the cross-correlation between the first and second points 402 and 404, and line 410 represents the cross-correlation between the second and third points 406 and 408 over time. Similarly in FIG. 5D, line 508 represents the cross-correlation between the first and second points 502 and 504 shown in FIGS. 5A and 5B, and line 510 represents the cross-correlation between the second and third points 506 and 508 over time. As shown in FIG. 4D, cross-correlation values are relatively high between each lateral pair within the homogenous medium. By contrast, cross-correlation values are much lower for line 510 in FIG. 5D, indicating the likely presence of a lesion between points 504 and 506 in the heterogeneous medium. By comparing the amplitude displacement and cross-correlation values to corresponding reference values, systems herein are configured to reconstruct qualitative representations of tissue elasticity, shown in FIGS. 6A and 6B, that unlike quantitative maps based on shear wave time-of-flight, do not require high shear-wave displacement SNRs. In various embodiments, all amplitude displacement determinations made by the qualitative processing module 140, including with respect to the reference maps, are normalized with respect to the maximum displacement volume, thus providing an accurate depiction of relative tissue elasticity changes based on differences in displacement amplitude.

In certain aspects, a reference map may be generated using measured correlation values for a pixel as compared to a reference correlation value, which corresponds to the medium being assessed. For example, correlation-coefficients of shear waves at neighboring spatial locations are utilized for mapping spatial stiffness distributions. Such a map can be referred to as a decorrelation map, since maximum correlation is observed in the case of no inclusion, and any inclusion detection is based on the loss of correlation, hence the name decorrelation. While a "traditional" map based on shear displacement amplitudes is sensitive to the changes in the wave amplitude only, a change in the correlation-coefficient (decorrelation) between displacement profiles in two spatial points is also sensitive to the changes of wave shape and frequency, therefore a higher sensitivity to the changes in the material properties can be achieved. This higher sensitivity is essential for lesion detection and monitoring in the case of low displacement amplitude and low SNR. Also, a reference map is obtained experimentally and measured correlation values for a pixel are then divided by the reference correlation value to get the loss of correlation due to the differences in the tissue stiffness compared to the homogeneous medium. The decorrelation value of a pixel located in $(x_o, y_o)$ is given as $$C(x_0, y_0) = \frac{D(x_{0+1}, y_0) \star D(x_o, y_0)}{D_{ref}(x_{0+1}, y_0) \star D_{ref}(x_o, y_0)} \quad (1)$$

where ★ indicates the cross-correlation operator between two signals, D(x,y) indicates the displacement signals as a function of time at the coordinate (x,y), measured for two consecutive points, and sub-script ref indicates a reference measurement. The calculated decorrelation maps are then displayed in decibel scale for better visualization.

Also, the comparison can be performed with a modified cross-correlation function *

$$(f \underline{\star} g)(\tau) \stackrel{*}{=} \int_{-T}^{T} f^*(t) g(t+\tau) dt, \quad (3)$$

which limits the integration range to suitably chosen maximum time lag T, thus excluding potentially noisy parts of the signal at very early/late times.

Alternatively the limited integration range can be asymmetric, i.e. range from $T^{min}$ to $T^{max}$, with suitably chose values for the minimum and maximum of the integration time.

Alternatively, the comparison can be performed with weighted versions of the signals D and/or $D_{ref}$, by multiplying the functions D, $D_{ref}$ with suitably chosen weighting functions w before applying the cross-correlation operator in equation (1). One suitable weighting function to reduce noise from low signal levels away from the peak is a Gaussian function $$w(x) = ae^{-\frac{(x-b)^2}{2c^2}} \quad (4)$$

with arbitrary a as a scale parameter and constant b chosen such that the peak of the weighting function matches the peak of the expected signal D(x).

FIG. 6A is a shear wave displacement amplitude reconstruction map generated by comparing the data extracted from FIGS. 4C and 5C. The map includes an area of high amplitude variation 602a, with respect to a reference, indicating the likely presence of an ablation-induced lesion, surrounded by an area of comparably low amplitude variation 604a. FIG. 6B is a shear wave decorrelation reconstruction map generated by comparing the data extract from FIGS. 4D and 5D. The presence and approximate location of the ablation-induced lesion is corroborated by a localized region of high decorrelation 602b, surrounded by an area of comparably low decorrelation 604b, which align closely with the areas of high and low amplitude variation respectively shown in FIG. 6A. When generating the shear wave amplitude displacement reconstruction map of FIG. 6A and/or the shear wave decorrelation reconstruction map of FIG. 6B, one or more components herein, e.g., qualitative processing module 140 and/or display processor 148, can be configured to interpolate amplitude displacement/decorrelation values positioned between each of the laterally-spaced receive beams, thereby generating a smooth, spatially-continuous map across an entire coverage area.

To clearly elucidate the outer boundaries of one or more lesions identified in the qualitative reconstruction maps, system components herein, e.g., boundary module 158, may be configured to combine the qualitative maps, e.g., such as the maps of FIGS. 6A and 6B, with at least one quantitative elasticity map of the same region. Doing so can remove noise from the quantitative elasticity maps. Systems herein can thus be configured to generate improved elasticity data that omits the noisy, low SNR data typically found in quantitative elasticity maps and instead embodies defined lesion locations delineated by clear boundaries. In this manner, systems herein improve ultrasound SWI technology by removing noise, improving the accuracy of lesion identification, and reducing processing time.

Figure 7:
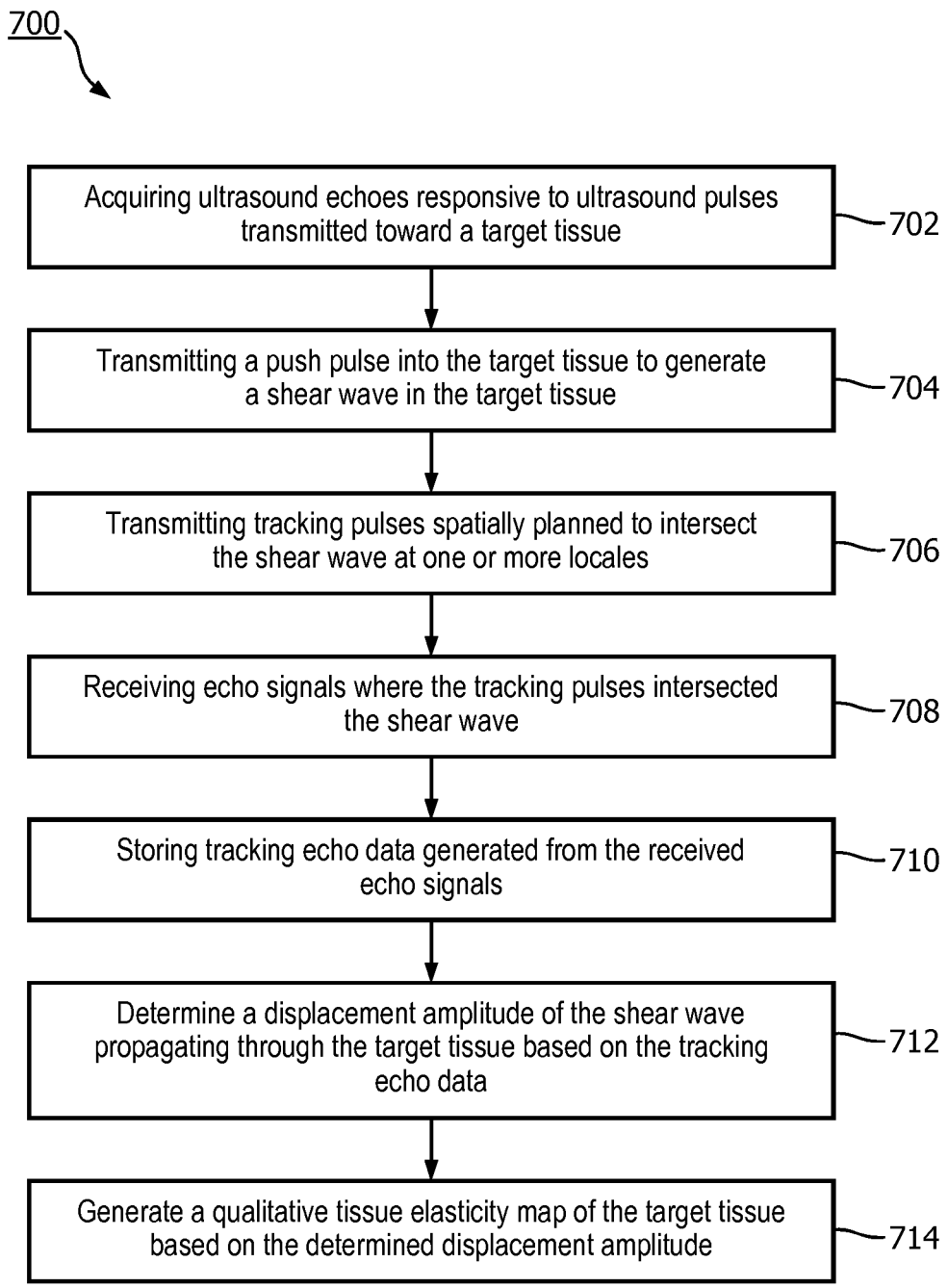
FIG. 7 is a flowchart showing a method performed in accordance with principles of the present disclosure.

FIG. 7 is a flow diagram of a method of shear wave imaging performed in accordance with principles of the present disclosure. The example method 700 shows steps that may be utilized, in any sequence, by the systems and/or apparatuses described herein. The method 700 may be performed by an ultrasound imaging system, such as system 100, or other systems including, for example, a mobile system such as LUMIFY by Koninklijke Philips N. V. ("Philips"). Additional example systems may include SPARQ and/or EPIQ, also produced by Philips.

In the embodiment show, the method 700 begins at block 702 by "acquiring ultrasound echoes responsive to ultrasound pulses transmitted toward a target tissue."

At block 704, the method involves "transmitting a push pulse into the target tissue to generate a shear wave in the target tissue."

At block 706, the method involves "transmitting tracking pulses spatially planned to intersect the shear wave at one or more locales."

At block 708, the method involves "receiving echo signals where the tracking pulses intersected the shear wave."

At block 710, the method involves "storing tracking echo data generated from the received echo signals."

At block 712, the method involves "determining a displacement amplitude of the shear wave propagating through the target tissue based on the tracking echo data."

At block 714, the method involves "generating a qualitative tissue elasticity map of the target tissue based on the determined displacement amplitude."

Figure 8C:
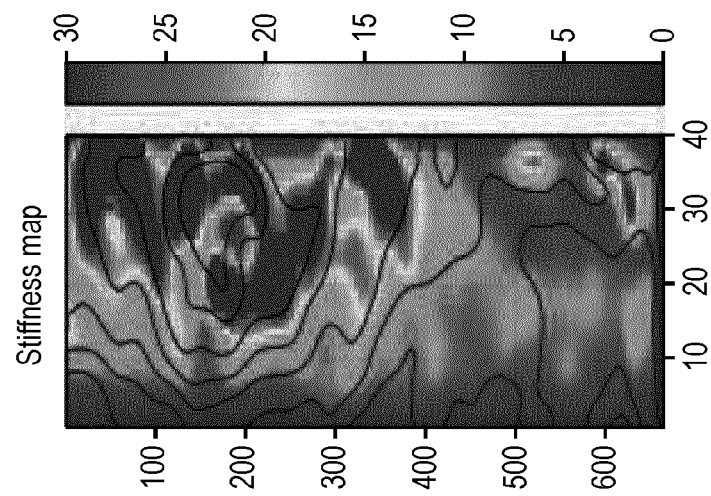
FIG. 8C is a quantitative elasticity map overlaid with the contour map of FIG. 8B.
Figure 8B:
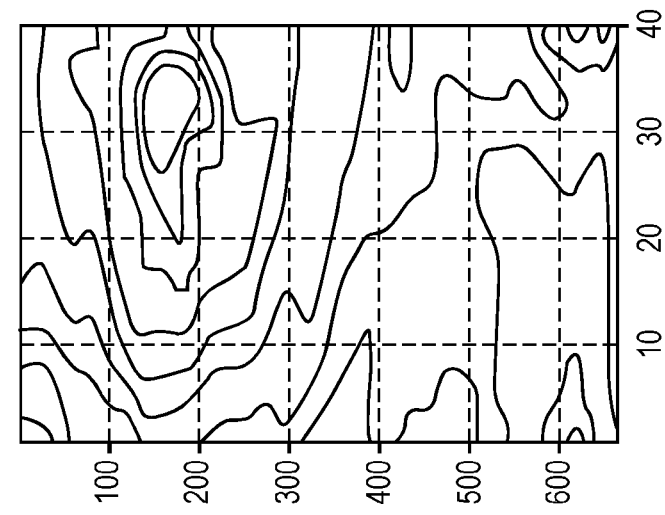
FIG. 8B is a contour map generated using the shear wave decorrelation reconstruction map of FIG. 8A.
Figure 8A:
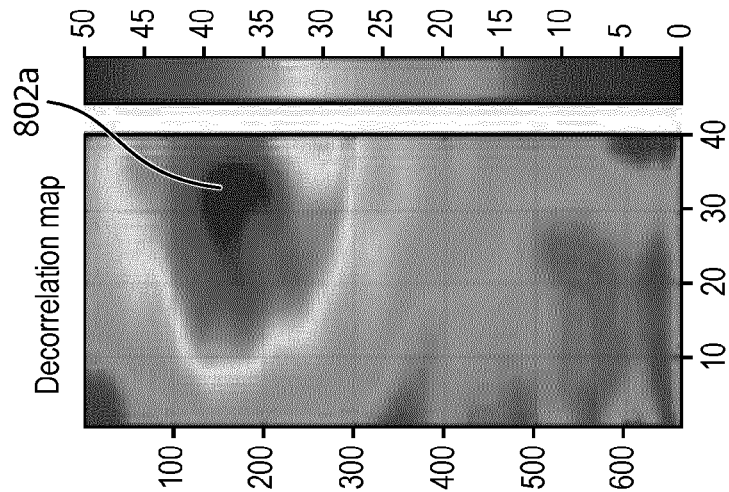
FIG. 8A is a shear wave decorrelation reconstruction map constructed in accordance with principles of the present disclosure.

FIG. 8A is an example of a shear wave decorrelation reconstruction map. Like the decorrelation map shown in FIG. 6B, the map of FIG. 8A is qualitative, and includes one localized region of high decorrelation 802a. Distinct regions of similar decorrelation can be discerned and grouped from the decorrelation reconstruction map by the boundary module 158, which can demarcate boundaries between each distinct region and generate contour lines to delineate them, thereby producing a decorrelation contour plot, as shown in FIG. 8B.

To enhance the accuracy of the contour lines with respect to the actual lesion boundaries, the boundary module 158 can also be configured to overlay the contour plot onto a quantitative tissue elasticity map, as shown in the overlay plot of FIG. 8C. The quantitative elasticity map may be generated in various ways described in the literature, e.g., according to a time-of-flight approach. As shown in FIG. 8C, the contour lines generated from the decorrelation map may not align precisely with the regions of distinct stiffness levels evident in the quantitative map. To assess and improve the fit between the contour plot and the quantitative elasticity map such that the contours encapsulate any focal lesions present in the underlying tissue with precision, two metrics can be generated by the boundary module 158. The first metric, focality (f), embodies the average stiffness distribution within a given contour with respect to the contour centroid. The second metric, penalty (p), embodies the average distribution of tissue stiffness outside the given contour. If a point (x,z) on the overlay plot is within a contour, the Young's modulus at that point will be contributed, by the boundary module 158, to the contour's focality. If the point lies outside the contour, the Young's modulus at that point will be contributed to the penalty for that contour. This relationship can be represented mathematically:

if $(x, z) \in C_i$, then $f = f + \dfrac{E(x, z)}{r}$ if not, then $p = p + \dfrac{E(x, z)}{r}$ E(x,z) indicates the stiffness value at a particular pixel location (x,z) at a distance r from the centroid of the area defined by the contour, and C, denotes the area enclosed by the contour at decorrelation dB level 'i.' The boundary module 158 can be configured to operate a cost function defined as the cost=p−f. To improve the fit between each contour line and a focal lesion included in the quantitative map, thereby generating an optimum contour line encompassing the lesion in some examples, the boundary module 158 can be further configured to minimize the cost function by maximizing the focality value and minimizing the penalty value for one or more candidate contour lines.

FIG. 9A is a graph of penalty 902, focality 904 and cost function 906 for a range of contour line candidate values (in decibels (dB)), produced from the qualitative decorrelation map of FIG. 9B. As shown, the cost function 906 initially decreases until reaching a minimum point at about 29 dB. The cost function 906 then increases as the penalty 902 term rises, indicative of an increasing number of pixels representing stiff tissue lying outside each contour line candidate encompassing a different cross-sectional area. The contour line at 29 dB represents the optimum contour line for the lesion 910 shown in FIG. 9B, as shown by the tight fit between the line 908 and the actual lesion when the line is overlaid on the decorrelation map in FIG. 9B. The optimum contour line 908 can also be overlaid onto the quantitative stiffness map by the boundary module 158. As shown in FIG. 9C, this action may reveal areas of high stiffness that do not represent a lesion. Such areas may instead represent signal noise or structures of high stiffness that do not contribute to an actual lesion. To clearly delineate the actual lesion in the presence of noise, the boundary module 158 can be further configured to mask areas within the quantitative map that fall outside the optimum contour line, such as region 912, and generate a hybrid map in which such masked areas are masked on a display. With reference to FIG. 1, the hybrid map 166 shown includes a lesion 168 and a masked region 170. In the particular embodiment shown, only the lesion 168 is shown on the map 166. In additional examples, one or more areas of tissue elasticity variation may be retained on the map. For instance, the boundary module 158 alone or in combination with the boundary display processor 164 and/or user interface 150, can be configured to apply different masking thresholds to increase or decrease the detail represented in the final hybrid map 166.

Figure 10A:
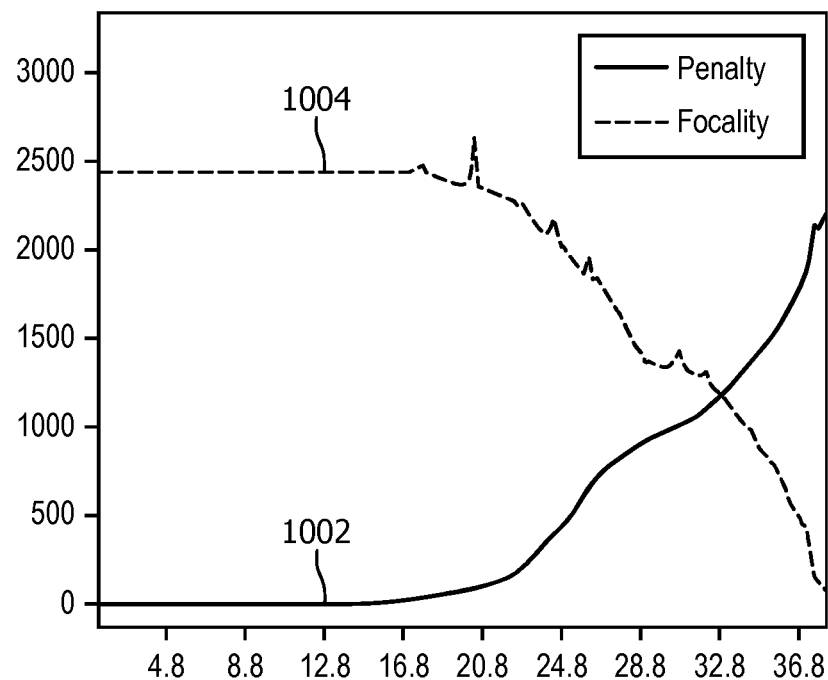
FIG. 10A is a graph of best fit metrics applied to candidate contour lines demarcating a lesion according to principles of the present disclosure.
Figures 10B, 10C, 10D:
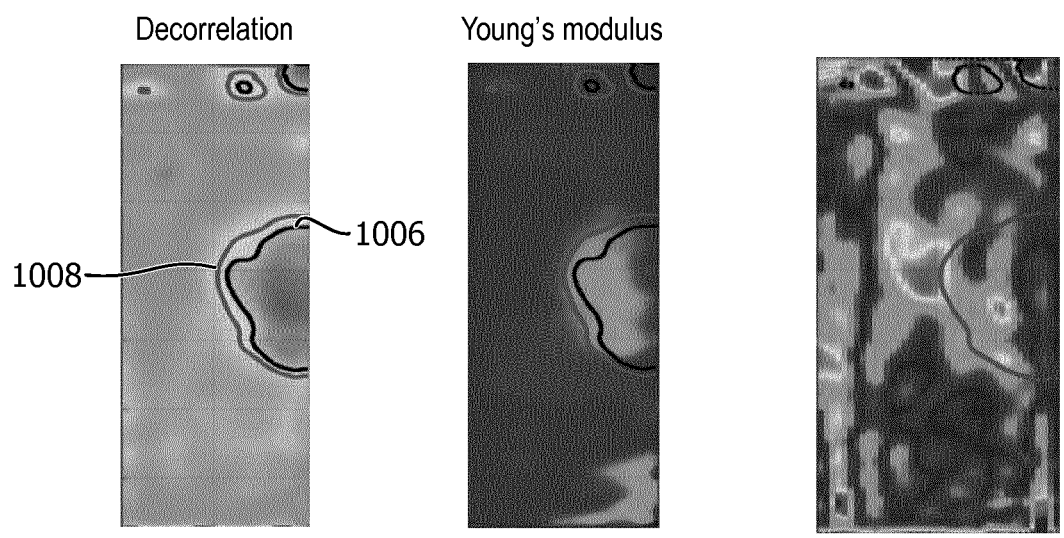
FIG. 10B is a shear wave decorrelation reconstruction map overlaid with candidate optimum contour lines.
FIG. 10C is a quantitative elasticity map overlaid with the candidate optimum contour lines shown in FIG. 10B.
FIG. 10D is a tissue elasticity gradient map overlaid with a candidate optimum contour line.

In some examples, the boundary module 158 can apply a maximum operator to the penalty function and the focality function to define the cost function, and proceed to identify the contour line that minimizes the cost function. According to such implementations, the cost function will be minimized at the intersection point of the penalty and focality functions, as shown in FIG. 10A. At about 32.8 dB, the penalty function 1002 intersects the focality function 1004. This contour threshold value is indicated by a first optimum contour line 1006 displayed on the qualitative decorrelation map of FIG. 10B. Alternatively, the optimum contour line can be determined based, at least in part, on the gradient of the qualitative decorrelation map, which is shown in the gradient map of FIG. 10D. To identify the optimum contour line based on gradient, a range of contour lines can be drawn onto the gradient map and for each line, the gradient values can be added together and the sum divided by the length of the contour line, thereby yielding the average gradient of each line. The contour line with the maximum average gradient can be selected and overlaid onto the decorrelation and/or quantitative stiffness map, as shown by the line 1008 in FIGS. 10B and 10C. The boundary will thus demarcate the most significant gradient change. In various examples, the boundary module 158 may be configured to evaluate two or more candidate contour lines, such as lines 1006 and 1008, and select one for demarcation of the lesion. A confidence level may be calculated for each line, and the line having the highest confidence level selected. In addition or alternatively, two or more candidate contour lines may be displayed for selection by a user. The user may select a single contour line based on visual evaluation of the candidates and/or by applying pre-set criteria. In some examples, the criteria may include a programmed preference for tissue over-inclusiveness, thereby decreasing the likelihood not ablating targeted tissue. By contrast, the criteria may also include a programmed preference for tissue under-inclusiveness, thereby minimizing the likelihood of ablating healthy tissue.

In some embodiments, the SNR may be too low to obtain a meaningful quantitative stiffness map. In such cases, the boundary module 158 may be configured to determine penalty and focality functions on a heat map or an elasticity map derived from a thermal model of an ablation process. According to such implementations, qualitative decorrelation maps can be substantiated by the quantitative thermal data.

Figure 11:
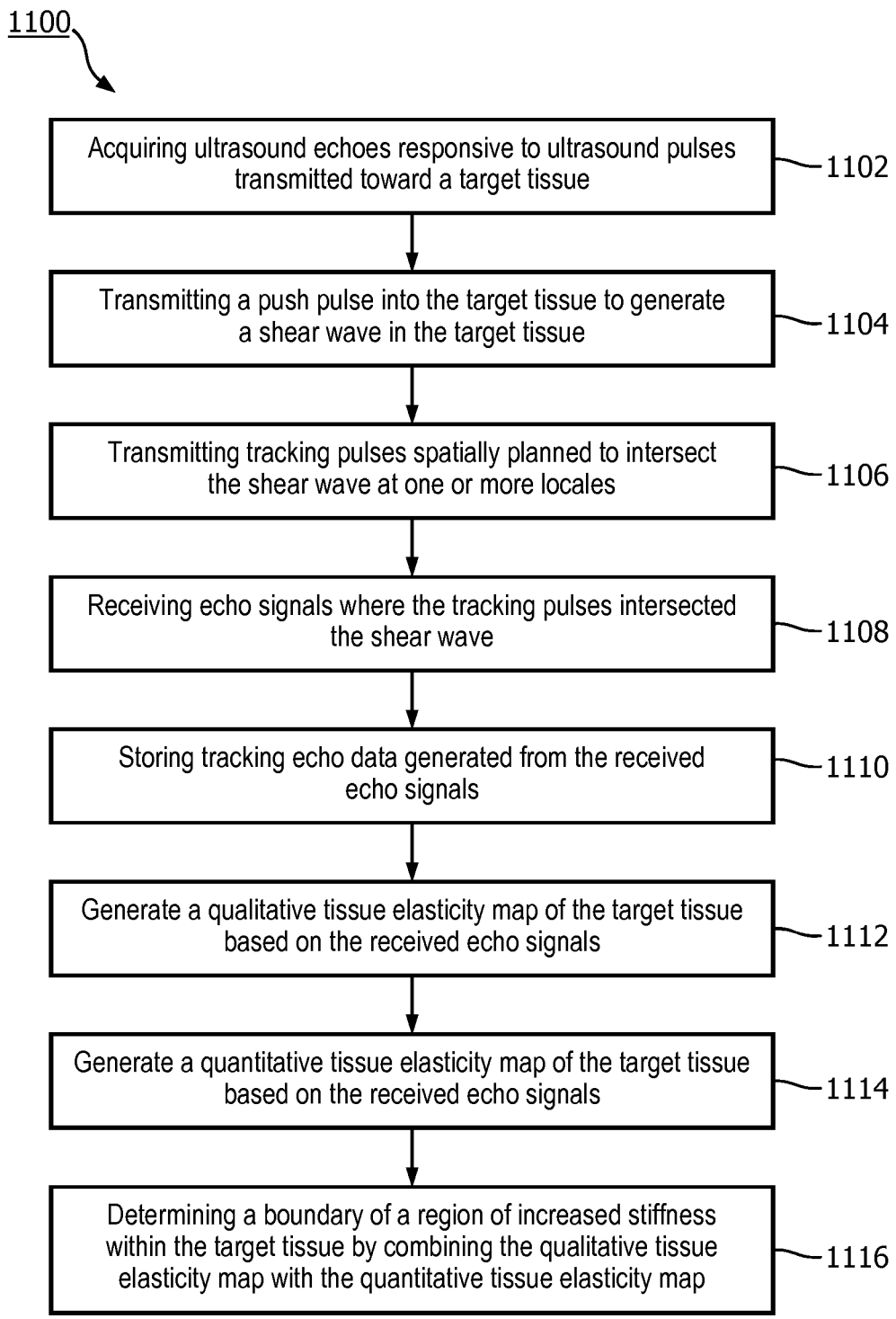
FIG. 11 is a flowchart showing a method performed in accordance with principles of the present disclosure.

FIG. 11 is a flow diagram of a method of shear wave imaging performed in accordance with principles of the present disclosure. The example method 1100 shows steps that may be utilized, in any sequence, by the systems and/or apparatuses described herein. The method 1100 may be performed by an ultrasound imaging system, such as system 100, or other systems including, for example, a mobile system such as LUMIFY by Koninklijke Philips N. V. ("Philips"). Additional example systems may include SPARQ and/or EPIQ, also produced by Philips.

In the embodiment show, the method 1100 begins at block 1102 by "acquiring ultrasound echoes responsive to ultrasound pulses transmitted toward a target tissue."

At block 1104, the method involves "transmitting a push pulse into the target tissue to generate a shear wave in the target tissue."

At block 1106, the method involves "transmitting tracking pulses spatially planned to intersect the shear wave at one or more locales."

At block 1108, the method involves "receiving echo signals where the tracking pulses intersected the shear wave."

At block 1110, the method involves "storing tracking echo data generated from the received echo signals."

At block 1112, the method involves "generating a qualitative tissue elasticity map of the target tissue based on the received echo signals."

At block 1114, the method involves "generating a quantitative tissue elasticity map of the target tissue based on the received echo signals."

At block 1116, the method involves "determining a boundary of a region of increased stiffness within the target tissue by combining the qualitative tissue elasticity map with the quantitative tissue elasticity map."

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for shear wave imaging comprising:
    an ultrasound transducer configured to acquire echoes responsive to ultrasound pulses transmitted toward a target tissue;
    a beamformer configured to:
    transmit, from the ultrasound transducer, tracking pulses in response to a push pulse, wherein the push pulse generates a shear wave in the target tissue and the tracking pulses are spatially planned to intersect the shear wave at one or more locales; and
    receive, from the ultrasound transducer, echo signals where the tracking pulses intersected the shear wave; and
    a processor in communication with the beamformer and configured to:
    store tracking echo data generated from the received echo signals;
    in response to the tracking echo data, determine a displacement amplitude of the shear wave propagating through the target tissue, wherein the determined displacement amplitude is determined at two or more laterally-spaced points within the target tissue; and
    based on the determined displacement amplitude, generate a qualitative tissue elasticity map of the target tissue by comparing the determined displacement amplitude to a reference displacement amplitude,
    wherein the reference displacement amplitude is determined at two or more laterally-spaced points within a reference tissue or is determined numerically from a simulated model, and
    wherein the processor is further configured to:
    determine a displacement amplitude decorrelation value by comparing the determined displacement amplitude at consecutive pairs of the laterally-spaced points within the target tissue;
    determine a reference displacement amplitude decorrelation value by comparing the determined displacement amplitude at consecutive pairs of the laterally-spaced points within the reference tissue;
    compare the displacement amplitude decorrelation value to the reference displacement amplitude decorrelation value; and
    based on the decorrelation value comparison, generate the qualitative tissue elasticity map.

2. The ultrasound imaging system of claim 1, wherein the reference tissue comprises a phantom model of the target tissue.

3. The ultrasound imaging system of claim 1, wherein the reference tissue comprises a patient sample of a tissue type corresponding to the target tissue and lacking a region of increased stiffness.

4. The ultrasound imaging system of claim 1, wherein the ultrasound transducer is coupled to an ablation device, the ablation device configured to ablate a region of increased stiffness or a larger region comprising the region of increased stiffness.

5. The ultrasound imaging system of claim 4, wherein the ultrasound transducer, beamformer and processor are configured to operate concurrently with the ablation device.

6. The ultrasound imaging system of claim 1, further comprising a user interface configured to display the qualitative tissue elasticity map.

7. The ultrasound imaging system of claim 1, wherein the reference displacement amplitude is derived from a reference map.

8. The ultrasound imaging system of claim 7, further comprising a memory configured to store a plurality of reference maps.

9. The ultrasound imaging system of claim 1, wherein the target tissue comprises a region of increased stiffness comprised of a thermal lesion.

10. The ultrasound imaging system of claim 1, wherein comparing the determined displacement amplitude to the reference displacement amplitude includes detecting an attenuation variation based on a peak-to-peak difference between the determined displacement amplitude and the reference displacement amplitude.

11. A method of shear wave imaging, the method comprising:
acquiring ultrasound echoes responsive to ultrasound pulses transmitted toward a target tissue;
transmitting a push pulse into the target tissue to generate a shear wave in the target tissue;
transmitting tracking pulses spatially planned to intersect the shear wave at one or more locales;
receiving echo signals where the tracking pulses intersected the shear wave;
storing tracking echo data generated from the received echo signals;
determining a displacement amplitude of the shear wave propagating through the target tissue based on the tracking echo data, wherein the determined displacement amplitude is determined at two or more laterally-spaced points within the target tissue; and
generating a qualitative tissue elasticity map of the target tissue based on the determined displacement amplitude,
wherein generating the qualitative tissue elasticity map of the target tissue based on the determined displacement amplitude comprises comparing the determined displacement amplitude to a reference displacement amplitude,
wherein the reference displacement amplitude is determined at two or more laterally-spaced points within a reference tissue or is determined numerically from a simulated model, and
wherein generating the qualitative tissue elasticity map further comprises:
determining a displacement amplitude decorrelation value by comparing the determined displacement amplitude at consecutive pairs of the laterally-spaced points within the target tissue;
determining a reference displacement amplitude decorrelation value by comparing the determined displacement amplitude at consecutive pairs of the laterally-spaced points within the reference tissue;
comparing the displacement amplitude decorrelation value to the reference displacement amplitude decorrelation value; and
based on the comparison, generating the qualitative tissue elasticity map.

12. The method of claim 11, further comprising displaying the qualitative tissue elasticity map on a user interface.

13. The method of claim 11, wherein the reference displacement amplitude is derived from a reference map.

14. The method of claim 11, wherein the target tissue comprises a region of increased stiffness comprised of a thermal lesion.

15. A non-transitory computer-readable medium comprising executable instructions, which when executed cause a processor of an ultrasound imaging system to:
acquire ultrasound echoes responsive to ultrasound pulses transmitted toward a target tissue;
transmit a push pulse into the target tissue to generate a shear wave in the target tissue;
transmit tracking pulses spatially planned to intersect the shear wave at one or more locales;
receive echo signals where the tracking pulses intersected the shear wave;
store tracking echo data generated from the received echo signals;
determine a displacement amplitude of the shear wave propagating through the target tissue based on the tracking echo data, wherein the determined displacement amplitude is determined at two or more laterally-spaced points within the target tissue; and
generate a qualitative tissue elasticity map of the target tissue based on the determined displacement amplitude,
wherein generating the qualitative tissue elasticity map of the target tissue based on the determined displacement amplitude comprises comparing the determined displacement amplitude to a reference displacement amplitude,
wherein the reference displacement amplitude is determined at two or more laterally-spaced points within a reference tissue or is determined numerically from a simulated model, and
wherein generating the qualitative tissue elasticity map further comprises:
determining a displacement amplitude decorrelation value by comparing the determined displacement amplitude at consecutive pairs of the laterally-spaced points within the target tissue;
determining a reference displacement amplitude decorrelation value by comparing the determined displacement amplitude at consecutive pairs of the laterally-spaced points within the reference tissue;
comparing the displacement amplitude decorrelation value to the reference displacement amplitude decorrelation value; and
based on the comparison, generating the qualitative tissue elasticity map.

* * * * *